(12) United States Patent  
Rivard et al.

(10) Patent No.: US 9,376,627 B2  
(45) Date of Patent: Jun. 28, 2016

(54) ORE FROTH PROCESSING

(71) Applicant: The Governors of the University of Alberta, Edmonton (CA)

(72) Inventors: Benoit Rivard, Edmonton (CA); Michael George Lipsett, Edmonton (CA); Jilu Feng, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 512 days.

(21) Appl. No.: 13/913,983

(22) Filed: Jun. 10, 2013

(65) Prior Publication Data

US 2013/0327683 A1 Dec. 12, 2013

Related U.S. Application Data

(60) Provisional application No. 61/657,431, filed on Jun. 8, 2012.

(51) Int. Cl.
| | |
|---|---|
| *C10G 1/04* | (2006.01) |
| *C10G 1/00* | (2006.01) |
| *G01J 3/42* | (2006.01) |
| *G01J 3/28* | (2006.01) |
| *G01N 21/31* | (2006.01) |
| *G01N 21/359* | (2014.01) |

(52) U.S. Cl.
CPC .............. *C10G 1/008* (2013.01); *C10G 1/045* (2013.01); *G01J 3/28* (2013.01); *G01J 3/42* (2013.01); *G01N 21/31* (2013.01); *G01N 21/359* (2013.01); *G01N 2201/129* (2013.01)

(58) Field of Classification Search
CPC .......... C10G 1/008; C10G 1/045; G01J 3/28; G01J 3/42; G01N 21/31; G01N 21/359; G01N 2201/129
See application file for complete search history.

(56) References Cited

U.S. PATENT DOCUMENTS

| | | | |
|---|---|---|---|
| 4,433,239 A | | 2/1984 | Thompson |
| 6,768,115 B2 | | 7/2004 | Mikula et al. |
| 7,067,811 B2 | | 6/2006 | Long et al. |
| 7,399,406 B2 | | 7/2008 | Mikula et al. |
| 2003/0015663 A1* | | 1/2003 | Mikula .............. G01N 21/3563 250/339.11 |

OTHER PUBLICATIONS

B. Rivard et al. "Bitumen Content Estimation of Athabasca Oil Sand From Broad Band Infrared Reflectance Spectra"; The Canadian Journal of Chemical Engineering; vol. 88; Oct. 2010; p. 830-838.
Benoit Rivard and Michael Upset Infrared Spectroscopy for the Assessment of Oil Sand Froth Quality Paper delivered at Centre for Oil Sands Innovation at the University of Alberta; Jun. 2011; p. 1-37.

(Continued)

*Primary Examiner* — Mark R Gaworecki
(74) *Attorney, Agent, or Firm* — Anthony R. Lambert (57) ABSTRACT

Apparatus and method for processing ore, the method comprising obtaining a reflectance spectra of an ore froth using a camera, applying a calculation using at least a wavelet decomposition to the reflectance spectra and generating a value representative of the reflectance spectra of the ore froth, classifying the quality of the ore froth using the value, and using the classification of the quality of the ore froth in froth processing.

19 Claims, 8 Drawing Sheets

(56) References Cited

OTHER PUBLICATIONS

B. Rivard, J. Feng, A. Gallie, A. Sanchez-Azofeifa; "Continuous Wavelets for the Improved Use of Spectral Libraries and Hyperspectral Data"; Remote Sensing of Environment 112 (2008), p. 2850-2862.

D. Lyder; J. Feng; B.Rivard; A. Gallie; E. Cloutis: Remote Bitumen Content Estimation of Athabasca Oil Sand From Hyperspectral Infrared Reflectance Spectra Using Gaussian Singlets and Derivative of Gaussian Wavelets; Fuel: the Science of Technology of Fuel and Energy; vol. 89; Issue 3; Mar. 2010; ISSN 0016-2361; p. 760-767.

* cited by examiner

ORE FROTH PROCESSING

CROSS-REFERENCE TO RELATED APPLICATIONS

This application claims the benefit under 35 USC 119(e) of U.S. provisional application Ser. No. 61/657,431 filed Jun. 8, 2012, which is hereby incorporated by reference in its entirety.

TECHNICAL FIELD

Ore Froth Processing.

BACKGROUND

This document describes the use of spectra collected from ore froth to predict properties of froth quality and properties of the ore from which the froth was produced for example froth color, solid to bitumen ratio, froth ore processability, fines content, and total bitumen content, and to use this information in process control. This disclosure describes flotation implementation and collection of spectra, the preprocessing of spectra, the spectra features sensitive to each of the three properties and the related predictive models, and implementation of the method.

The separability of bitumen from oil sand depends on a number of factors. Some of these factors are observable using reflectance spectrometry. This document describes bitumen recovery performance tests conducted using a Denver cell for water flotation of aerated bitumen froth under a standard set of operating conditions. Further, hyperspectral measurements of ore samples and oil froth are described. Features associated with bitumen, quartz, and clay readily visible in samples and in the froth at the surface of the cell are described. We disclose the use of spectral information to predict the total bitumen content, fines content, solid to bitumen ratio and processability of ore samples, the relationship of these variables to froth colour, and the techniques of classifying froth types using spectra.

Naturally occurring oil sand may be a mixture of quartz grains, clay minerals, bitumen, and water. Bitumen recovery performance, termed processability (ore processability being the expected fraction of product material that may be separated using a particular separation circuit—a measure of the expected recovery of product material for a particular process), may depend on bitumen content, types and amounts of clays present, degree of weathering of the ore before processing, and process conditions for a given process configuration. As ore deposits are not homogeneous and ore may display considerable variability in clay, bitumen, water and fines, which impact the bitumen recovery and processability, there is a need for a robust method to characterize processability of incoming feed stock in near real-time prior to reaching the plant.

The high-precision ($\leq 0.5\%$) determination of total bitumen content (TBC) in oil sand ore is typically conducted by traditional analytical approaches that are time consuming (several hours per sample). Infrared reflectance spectroscopy has been used in a number of oil sand studies to investigate for example variations in oil sand slurry, the mineralogy of oil sands, bitumen characteristics, and bitumen content in ground ore. In past studies [1], [2] we used reflectance spectra of oil sands to generate predictive models of total bitumen content and fines content. This work discloses by contrast, the relationship between spectral properties of oil sand ore froth and observations of ore processability, to assist in improving the processability of the incoming feedstock ore in real time before it enters the extraction plant.

SUMMARY

A method of processing ore froth comprising obtaining a reflectance spectra of an ore froth using a camera, applying a calculation to the reflectance spectra to generate a value representative of the reflectance spectra of the ore froth, classifying the quality of the ore froth using the value and using the classification of the quality of the ore froth in ore froth processing.

An ore processing apparatus comprising a camera directed towards a vessel containing ore froth, a computer apparatus configured as a classifier for applying a calculation to the reflectance spectra to generate a value representative of the reflectance spectra of the ore froth and classifying the quality of the ore froth using the value and a display for displaying the value.

A method of monitoring ore froth processing comprising obtaining a reflectance spectra of an ore froth using a camera, applying a calculation to the reflectance spectra to generate a value representative of the reflectance spectra of the ore froth, classifying the quality of the ore froth using the value to generate an output and displaying the output to a user.

These and other aspects of the device are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Immaterial modifications may be made to the embodiments described here without departing from what is covered by the claims. The specific embodiments disclosed are exemplary and not intended to limit the generality of the claims.

Figure 3:
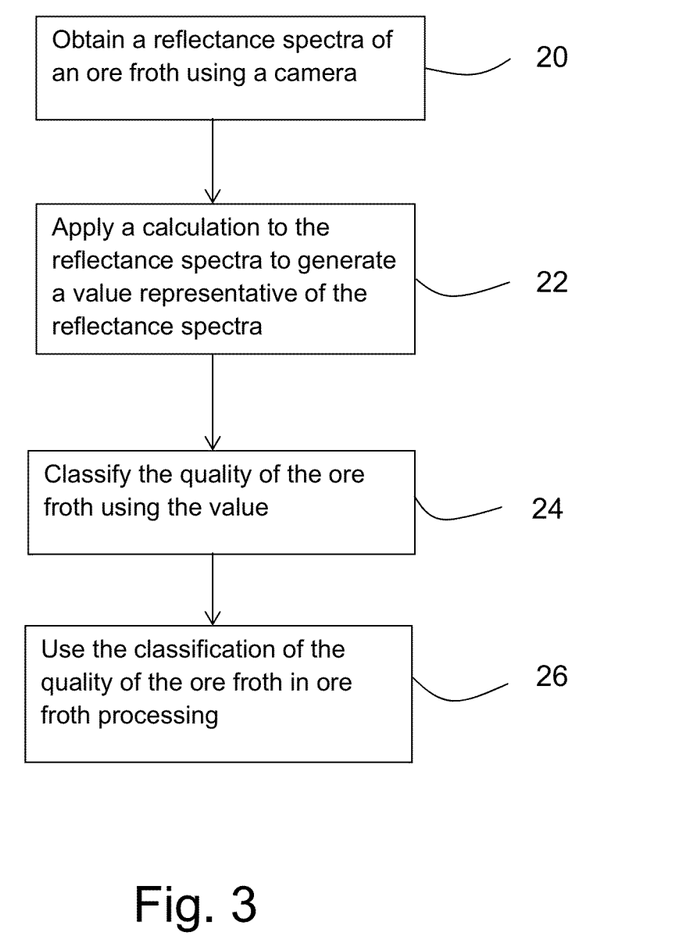
FIG. 3 is a block diagram showing the process steps in an embodiment.
Figure 4:
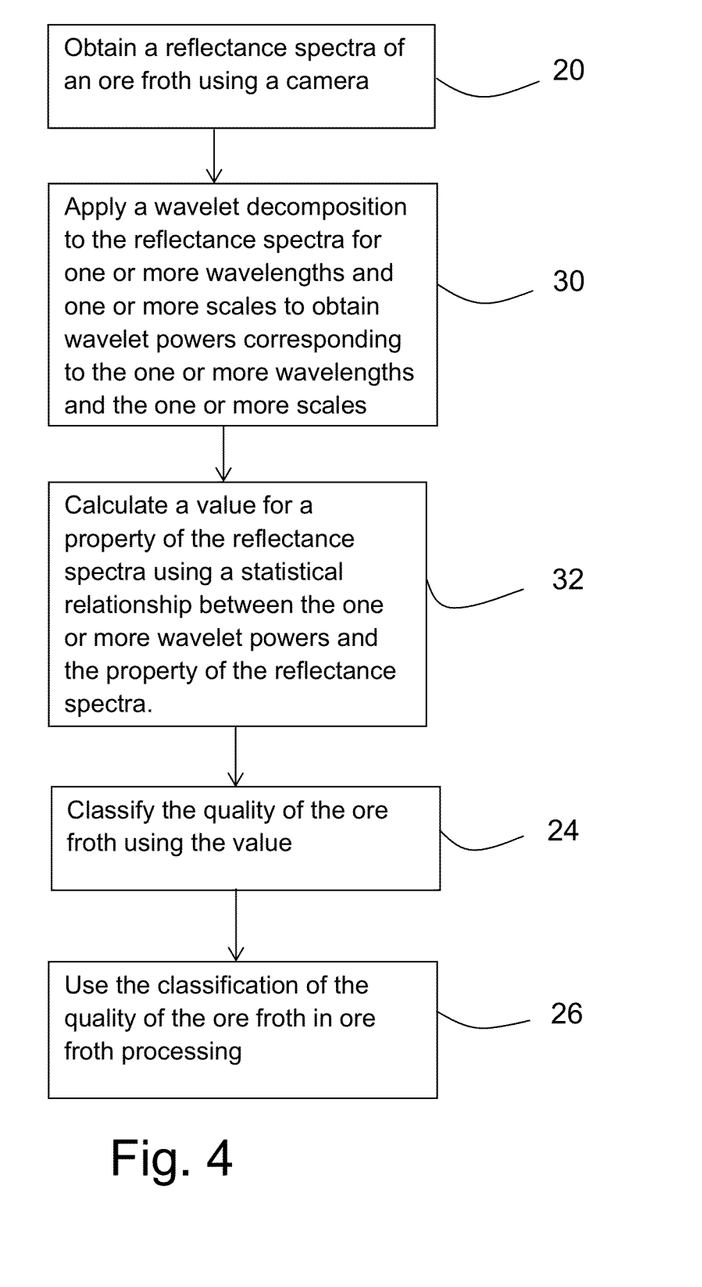
FIG. 4 is a block diagram showing the process steps in an embodiment in which wavelet decomposition is used.

To achieve this goal, as shown in FIG. 3 we disclose a method of processing ore froth, the method comprising obtaining a reflectance spectra of an ore froth using a camera as shown in step 20; applying a calculation to the reflectance spectra to generate a value representative of the reflectance spectra of the ore froth as shown in step 22; classifying the quality of the ore froth using the value as shown in step 24; and using the classification of the quality of the ore froth in ore froth processing as shown in step 26. In one embodiment the froth is bitumen froth, but the method may be applied to other ore froth. In another embodiment, as shown in FIG. 4, the method comprises applying a wavelet decomposition to the reflectance spectra for one or more wavelengths and one or more scales to obtain wavelet powers corresponding to the one or more wavelengths and the one or more scales as shown in step 30 and calculating a value for a property of the reflectance spectra using a statistical relationship between the one or more wavelet powers and the property of the reflectance spectra as shown in step 32.

We disclose comparisons of our method to existing predictive models of bitumen and fines content for ten ore samples of varying processability. Our previous work has demonstrated that the heavy hydrocarbons in Athabasca oil sand have distinct spectral features in the shortwave and thermal infrared (7-12 microns) regions. The method disclosed here and the statistical relationship used to estimate total bitumen content, fines contents (percent particle passing at 44 microns (% pp 44) and percent sub-3.9 micron particle passing (% pp 3.9) (clay dominated)), processability, solid to bitumen ratio and color performed exceedingly well for the ten ore samples of variable processability (see for example Tables 5, 6, 7, 8 and 13, below). Spectra of froth may be classified into two classes that provide a broad metric of sample processability and that relate to visual color and fines content of the froth. The greater scatter of the data for the brown froth suggests that the brown froths are compositionally more variable and likely incorporate a range of mineral types and abundance. Mineralogical features from froth may be used to confirm the hyperspectral features and to relate froth features to flotation process kinetics. Such information may be valuable for process control.

There are several ways that this technique may be applied for process control. The simplest comprises using measurements of the top of the supernatant froth layer to observe process performance, and then use feedback control to reduce problematic effects. Spectral features from froth may be related to spectral features in ore, and may then be used in feed-forward process control. Because there are multiple processing steps and control actions in a continuous process plant, the relationship between feedstock properties and downstream separation performance may depend on much more than just ore spectral properties. In using this froth measurement technique for separation process control, the control actions may include adding additional reagents upstream, adding additional air upstream, changing froth underwash conditions, adding additional dilution water, recirculating low-quality froth back to the primary separation cell, reducing feed to increase residence time, and other standard interventions. Substandard material may still be processed to separate as much product material as possible. A feed-forward scheme based on ore spectra may allow for off-specification waste soil to be rejected from the mining process if unacceptable dilution of grade would occur.

During ore froth processing and ore froth process control, a threshold value may be used to determine the type of processing to be applied to the ore froth. The threshold value may be experimentally determined. A value associated with a property of the ore froth (the value being calculated by the method in this disclosure) may be incorporated into the process control system. By comparing the calculated value to the threshold value certain actions may be taken. For example, depending on the relationship of the calculated value to the threshold value the action may be adding additional reagents, adding additional air, changing froth underwash conditions, adding additional dilution water, recirculating low-quality froth back to a primary separation cell, reducing feed to increase residence time, rejecting off-specification waste soil, or another standard intervention. Furthermore, the calculated value may be incorporated into a continuous feedback control loop which results in similar actions as mentioned previously being taken.

Spectra may be measured at the top of the froth layer in various vessels such as a separation cell (such as a gravity settler), a mechanical flotation cell, hydrocyclone, or other separation unit that delivers froth to an intermediate holding tank. In another example, an autosampler may be used to withdraw a slipstream from the hydrotransport line ahead of the separation cell. Ore spectra may be acquired at several points.

Figure 2:
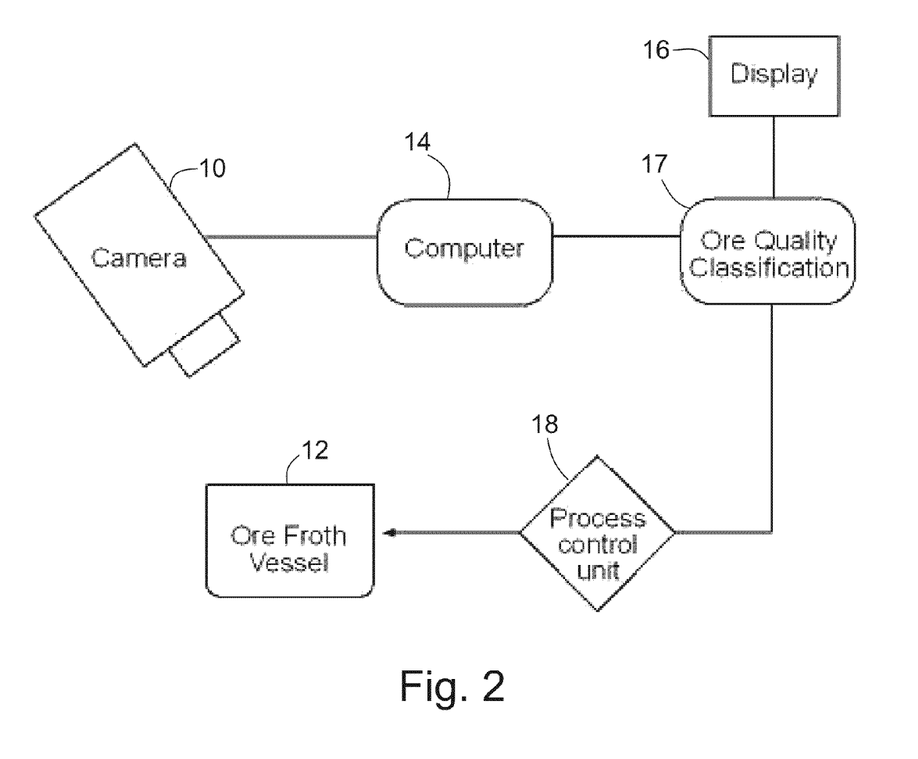
FIG. 2 is a block diagram of an ore froth processing apparatus.
Figure 8:
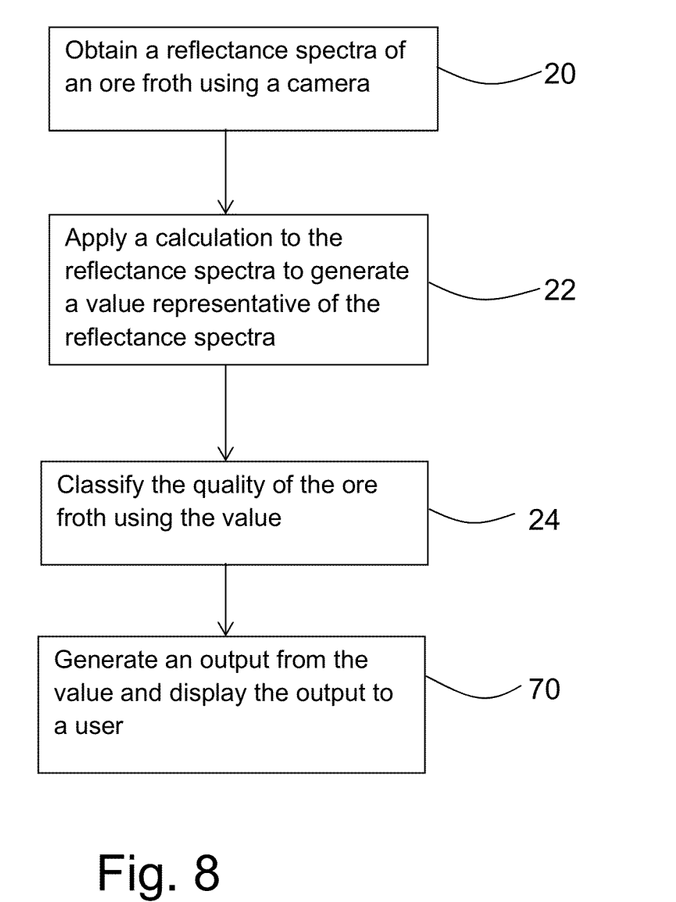
FIG. 8 is a block diagram showing process steps in an embodiment in which an output is displayed to a user.

The ore processing technique described in this disclosure may be implemented in an apparatus, shown in FIG. 2. The apparatus may use a camera 10 directed toward a vessel 12 such as described above containing ore froth. A computer apparatus 14 connected to the camera 10 may be configured as a classifier for applying a calculation to the reflectance spectra collected by the camera. The computer apparatus may be any conventional computer incorporating input and output devices, a processor and memory. The calculation generates a value representative of the ore froth. The computer apparatus then classifies the quality of the ore froth using this value in step 17. The value may be displayed on a display 16, as shown in step 70 of FIG. 8. A process control unit 18 may then respond to the computer apparatus for altering processing of the ore froth. The process control unit may be any conventional process control unit for the processing of ore froth.

A computer may be directed to carry out this ore processing technique using a non-transitory computer readable media, such as a disk, comprising instructions for carrying out the ore processing technique described in this disclosure.

1. Ore Samples and Froth Generation

Ten homogenized ore samples were selected with the expectation that the sample set would have a range of processability. Samples were stored in sealed 20 liter pails at a temperature of −15° C. to prevent oxidation as well as to prevent loss of water and aromatic components. Prior to spectral measurements, the samples were allowed to equilibrate to room temperature. Routine laboratory analyses were conducted to measure the bitumen, water, and solid contents in each sample. The bitumen content for the sample suite ranged from 6% to 14% (≤0.5% analytical error) and 2% to 10% water content.

Flotation experiments were conducted to rate the relative oil separation performance of the ten samples. A two-liter laboratory-scale Metso Denver flotation cell was used for the experiment. The temperature of the slurry inside the vessel was controlled by regulating the temperature of the water circulating in the jacket, and a thermometer was used to check the temperature of the slurry. Compressed air was introduced into the slurry and the air flow was controlled by air flow meter. Impeller speed (1500 rpm) and aeration rate (150 ml/min) were constant, following a standard protocol. Oil froth was extracted after twenty minutes for spectral measurement and visual color observation. The froth and ore were then separately analyzed in the laboratory using Dean Stark analysis to estimate the solid/bitumen ratio of the froth and the processability of the ore (Tables 11 and 12). During the flotation experiment, qualitative observations of froth color were also collected for each sample. See Table 4: ores with higher fine content (pp 44 μm) and lower bitumen content (<12%) tend to generate brown froth and have lower processability (Tables 14, 15, 16 and 17). Low fines content and higher bitumen content tend to generate dark froth with higher processability. Froth color is generally indicative of processability. Ore processability tends to relate to solid to bitumen ration and total bitumen content.

For example, sample 9 in this study produced black froth with excellent seperability, sample 4 produced a dark brown froth with good seperability and sample 6 produced brown froth with poor seperability;

2. Collection of Spectra

In a particular embodiment, reflectance spectra may be acquired using an Analytical Spectral Device Fieldspec FR spectrometer (ASDFR), which operates from 350-2500 nm. Other types of cameras or spectrometers may be used. The camera or infrared spectrometer may obtain spectra or images at other wavelengths. For example the camera may obtain infrared wavelength reflectance spectra, visible wavelength reflectance spectra, or both visible wavelength reflectance spectra and infrared wavelength reflectance spectra. In a particular embodiment, the light source may be a 50 W quartz halogen lamp, located at 30 deg from nadir. The sensor may be at nadir. Each spectrum may be taken within 1 second with 25 co-adds and 1 nm spectral resolution. The reflectance spectra may be obtained from the ratio of each sample measurement to that of an illuminated 99% reflectance panel taken with the same geometry. The instantaneous field of view for the oil sand ore and the froth may be a circle with a diameter of 20 mm and 15 mm, respectively. In a particular embodiment, the reflectance spectra comprises an average of a set of several reflectance spectra. For example the final spectra of each sample and froth may be generated by averaging six and three measured spectra, respectively, each obtained at a different location.

Figure 1:
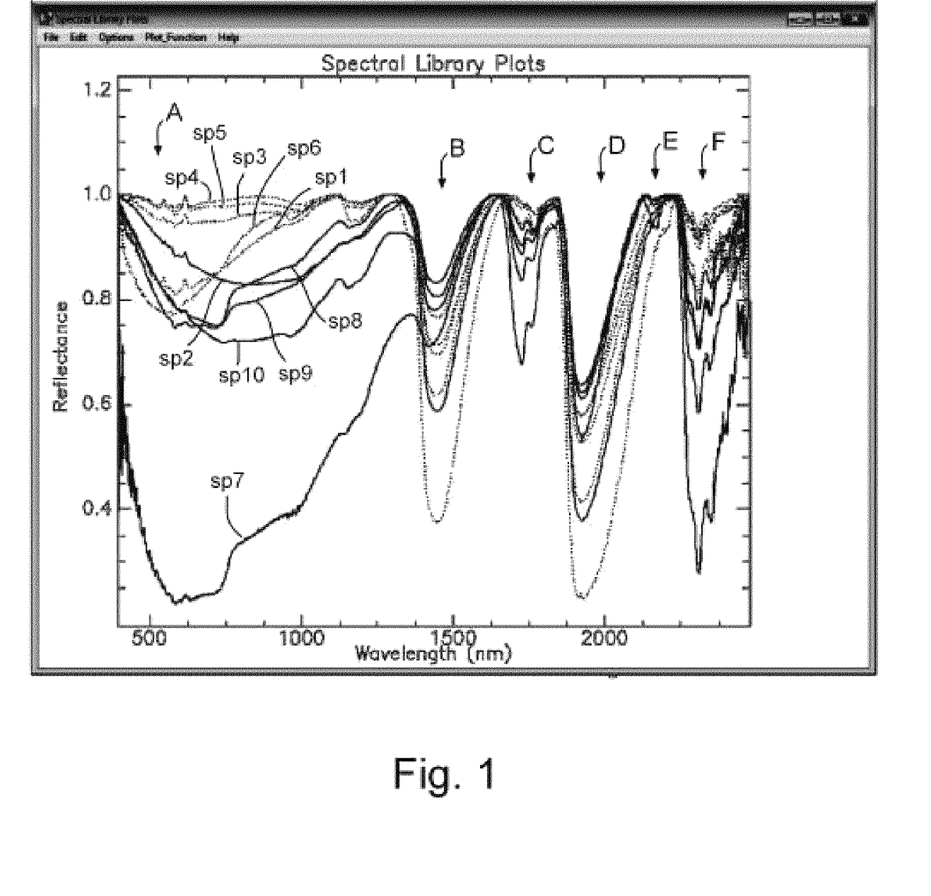
FIG. 1 is a spectra of the ten samples.

Referring to FIG. 1, showing the spectra of the ten samples (sp1 (MC09), sp2 (AN225), sp3 (AN397), sp4 (AN155), sp5 (AN178f96), sp6 (AQ09), sp7 (AN178f26), sp8 (AN229), sp9 (AN117) and sp10 (AN239), features of water (B, D), clay (E) and bitumen (C, F) may be present in the spectra. Froth colors, from dark to brown, may be roughly determined in visible region (A) and near-infrared region. Brown froths tend to have a lower bitumen fraction, which is best represented in the short wave infrared region.

3. Pre-Processing of Spectral Data

3.1. Spectral Decomposition

In a particular embodiment, a wavelet decomposition or transformation may be applied to the reflectance spectra. For example, continuous wavelet analysis (CWT) may be conducted on the spectra to improve the detection of spectral features, but various types of wavelet decomposition or transformation may be used depending on the application and may be determined using experimentation. Mathematical details on wavelet analysis may be found in our previous publications (Rivard et al. 2008 [3], Lyder et al. 2010 [1], Cheng et al. 2011 [4]). The general principle behind this technique is that any reflectance spectrum may be represented as a sum of similar wave-like functions (wavelets). As a first step, the mean reflectance of the spectrum calculated over the entire spectral range is subtracted at each band. This mean subtraction is required to ensure that the wavelets are comparable between scales, and that the wavelets from different spectra are comparable at the same scale.

The CWT is a linear operation that uses a mother wavelet function to convert a hyperspectral reflectance spectrum $f(\lambda)$ ($\lambda=1, 2, \ldots, n$), where n is the number of wavebands and n=2151 herein) into sets of coefficients. Mathematically, the continuous wavelets $\psi_{a,b}(\lambda)$ are produced by scaling (dilating) and shifting (translating) a mother wavelet $\psi(\lambda)$:

$$\psi_{a,b}(\lambda) = \frac{1}{\sqrt{a}}\psi\left(\frac{\lambda-b}{a}\right) \qquad (1)$$

where a and b are positive real numbers, a is the scaling factor defining the width of the wavelet, and b is the shifting factor determining the position. The output of CWT is given by:

$$W_f(a,b) = \langle f, \psi_{a,b}\rangle = \int_{-\infty}^{+\infty} f(\lambda)\psi_{a,b}(\lambda)d\lambda \qquad (2).$$

For all scales of decomposition, the CWT coefficients ($W_f(a_i,b_j)$, $i=1,2,\ldots,m$, $j=1,2,\ldots,n$) constitute a 2-dimensional scalogram (i.e. a m×n matrix) of which one dimension is scale ($1, 2, \ldots, m$) and the other is wavelength (or waveband, $1, 2, \ldots, n$). Each scale component of the scalogram is of the same length as the reflectance spectrum and this representation is readily interpretable. Low scale components are suitable to capture the characteristics of narrow absorption features and high scale components are well suited to define the overall spectral shape of spectra. The wavelet power, which refers to the magnitude of each wavelet coefficient, measures the correlation between the scaled and shifted mother wavelet and a segment of the reflectance spectrum and reflects the similarity of the local spectral shape to the mother wavelet. It may be used to identify the change in shape and depth of absorption features across spectra and record the spectral variation introduced a given sample property (e.g. bitumen content).

In a particular embodiment, the negative normalized second derivative of Gaussian (DOG) also known as the Mexican Hat or Ricker wavelet was used as the mother wavelet basis. However, various mother wavelets may be used as a basis depending on the application, and may be derived using experimentation. The effective support range of the Mexican Hat is $[-5, 5]$ for the scale $a=1$ and $[-5a_1, 5a_1]$ for $a=a_1$. The width of a scaled wavelet ($10a_1$) determines the number of wavebands that are to be convolved with the wavelet and attributed to the wavelet coefficient. Since the wavelet decomposition at a continuum of possible scales ($i=1, 2, \ldots, m$.) would be computationally expensive and lead to a large data volume, the dimensions of the scalogram may be reduced by decomposing the reflectance spectra at dyadic scales $2^1, 2^2, 2^3, \ldots,$ and $2^{10}$. The wavelet data resulting from each spectrum may be stored as a wavelet power scalogram with dimensions of power, wavelength, and scale.

3.2 Feature Selection from Correlation Scalograms

In a particular embodiment, the one or more wavelet powers used in the statistical relationship between the one or more wavelet powers and a property of the reflectance spectra correlates with the property of the reflectance spectra. The one or more wavelet powers used in the statistical relationship are strongly correlated with the property of the reflectance spectra.

Figure 5:
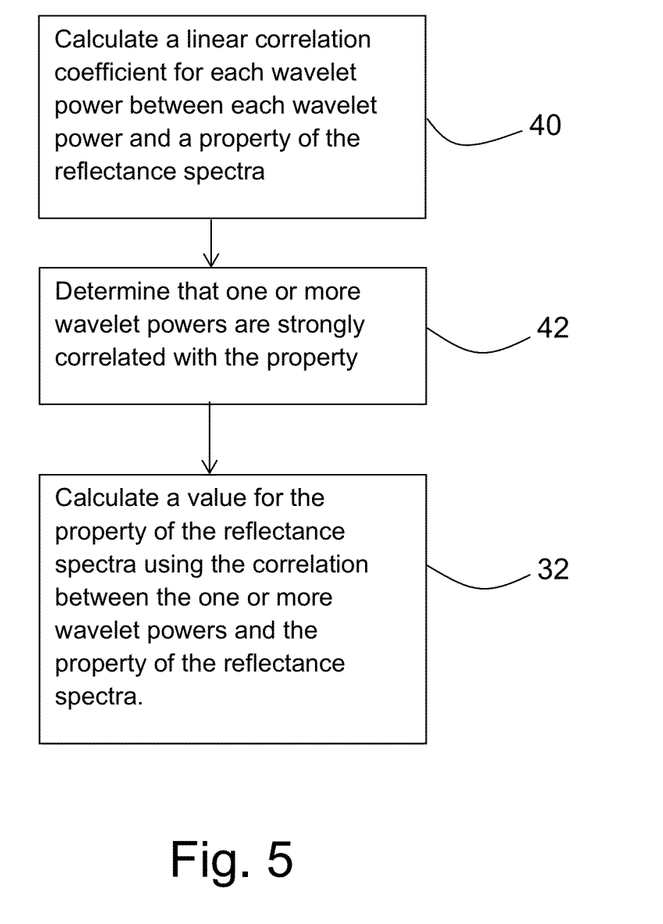
FIG. 5 is a block diagram showing process steps in an embodiment for calculating a correlation between one or more wavelet powers and a property of the reflectance spectra and using the correlation to calculate a value for the property of the reflectance spectra.

In a particular embodiment, as shown in FIG. 5, to identify wavelet powers strongly correlated to a property of interest for use in the statistical relationship, a correlation scalogram may be constructed by calculating a Pearson linear correlation coefficient for each wavelet power between each wavelet power and the property of interest as shown in step 40. The correlation scalogram reports a correlation coefficient (R), ranging in magnitude from 0 to 1, at each wavelength and scale. Each element of the correlation scalogram represents a wavelet power that may be selected. The features where R is not statistically significant ($p>=0.05$) may be masked. A threshold R may then be applied to the remaining features to isolate wavelength regions and wavelet powers of strongest correlation to the property of interest as shown in step 42. These wavelength regions may then be described with a center wavelength and full width half maximum using a wavelet power, and then used in the statistical relationship.

Figure 6:
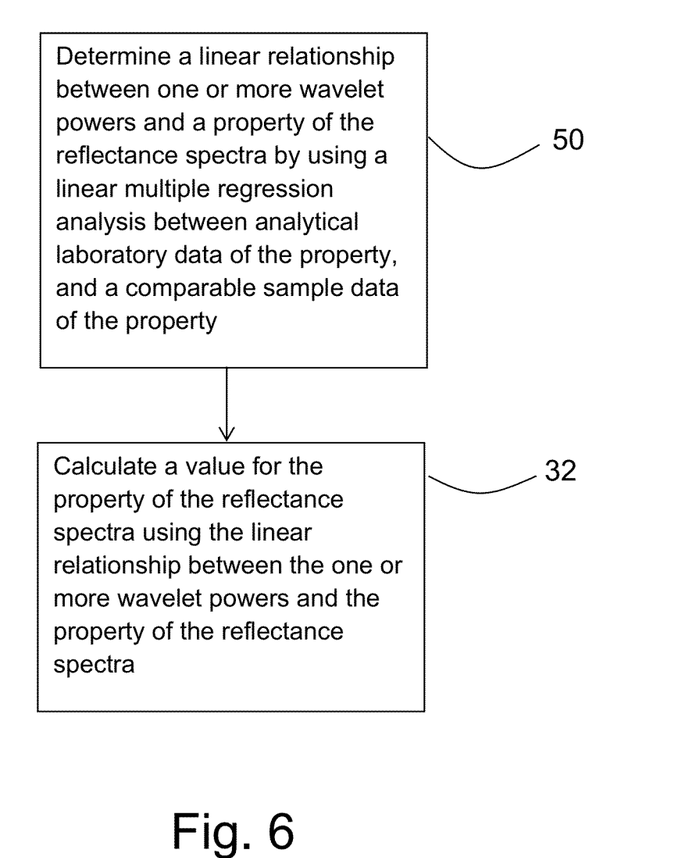
FIG. 6 is a block diagram showing process steps in an embodiment for determining a linear relationship between one or more wavelet powers and a property of the reflectance spectra and using the linear relationship to calculate a value for the property of the reflectance spectra.

In a particular embodiment, as shown in FIG. 6, the statistical relationship between the one or more wavelet powers and the property of the reflectance spectra may be a linear relationship. The linear relationship may for example be predetermined by using a linear multiple regression analysis between analytical laboratory data of the property, and a set of comparable sample data of the property as shown in step 50.

Figure 7:
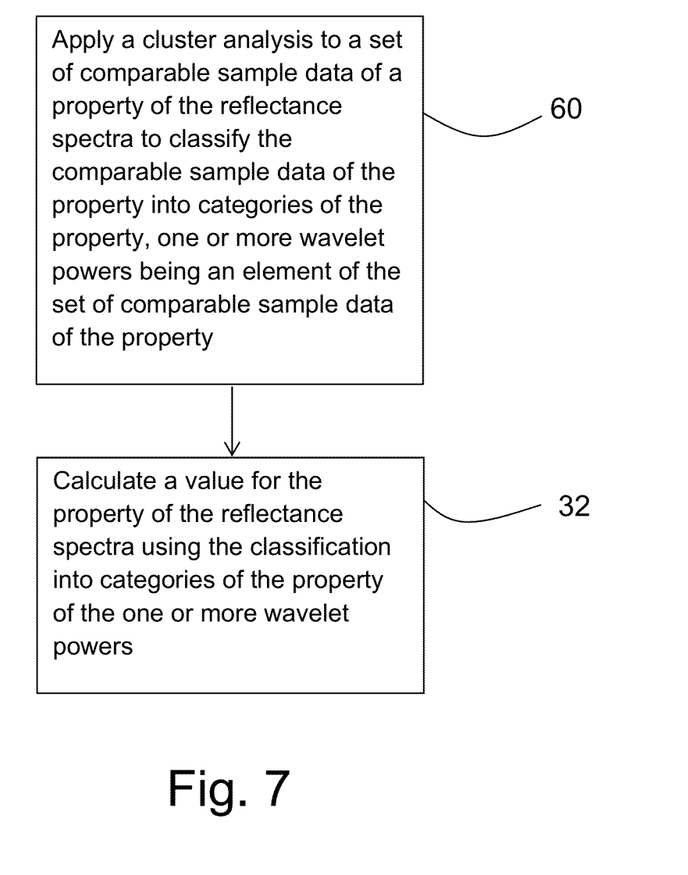
FIG. 7 is a block diagram showing process steps in an embodiment for classifying one or more wavelet powers into categories of a property of the reflectance spectra and using the classification into categories of the property to calculate a value for the property.

In another embodiment, as shown in FIG. 7, the statistical relationship between the one or more wavelet powers and the property of the reflectance spectra may be determined by applying a cluster analysis to a set of comparable sample data of the property of interest as shown in step 60. The cluster analysis classifies the comparable sample data of the property into categories of the property, the one or more wavelet powers are an element of the set of comparable sample data of the property. Thus the one or more wavelet powers may then be classified into a subset of the property of interest.

3.3 Continuum Remova

In another embodiment, applying a calculation to the reflectance spectra may further comprise continuum removal of the reflectance spectra. For example, for color analysis, the continuum may be removed from the spectra. A reflectance spectrum comprises a continuum and individual absorption features. The continuum may also be referred to as the baseline. The depth of an absorption band, D, may be defined relative to the continuum, $R_c$:

$$D = 1 - R_b/R_c \qquad (3)$$

where $R_b$ comprises the reflectance at the band center, and $R_c$ comprises the reflectance of the continuum at the same wavelength as $R_b$.

The continuum removal process requires minimal computation cost, and thus may have value for rapid spectral characterization of targets.

4. Application to the Prediction of Froth Quality

Froth quality may be determined by qualitative and quantitative parameters such as froth color (qualitatively categorized as black and brown as determined by a trained operator), and the solid to bitumen ratio (SBR) in froth, the later determined by Dean-Stark laboratory analysis of the froth for each sample.

4.1 Froth Color

Table 1 compiles visual observations of the color of the froth for each sample. Also shown is the laboratory measured percent passing of fines smaller than 44 microns (% pp 44), which is an industry-standard definition of fine solids. Samples with brown froth display a range of brown hues; and these correspond to the samples with the highest fines content (Table 1). Samples with dark froth show less froth color variability and are usually characterized by lower percentage of fines. Based on these observations, spectra of dark and brown froths were respectively assigned color class labels of 0 and 1 for spectral classification. This nominally corresponds to a percent fines threshold of 25%.

For spectral classification of froth spectra, the spectral continuum may be calculated from 400-2450 nm. After continuum removal, bands associated with water absorption (1301-1649 nm, 1751-2249 nm) may be excluded from further analysis. The resulting 10 continuum removed spectra may be classified into two categories using an unsupervised K-mean classifier. The preset number of categories may be set to two and number of iteration to one. The spectral regions for the classification may include 800-1300 nm, 1650-1750 nm, and 2250-2350 nm. The results show that all the spectra from black froth belong to one category, while spectra from brown froth belong to another with 100% accuracy.

A two-category classification of froth spectra was devised based on the color scheme defined above. Class ID=0 is for dark froths and samples with less than 25% fines; and class ID=1 is for brown froths and samples with more than 25% fines (Table 1). Continuous wavelet analysis was conducted to detect spectral features that correlate with the property. Seven features from the ASDFR spectra of froths were found to correlate with the property (correlation coefficient greater than 0.92).

The dark froths may be distinguished from the brown froths by employing a simple three-band composite of wavelet power at 937 nm, 2160 nm, and 2200 nm (Table 10). The dark froths cluster more tightly than the data for the brown froths. The greater scatter of the data for the brown froth suggests that the brown froths are compositionally more variable and likely incorporate a range of mineral types and abundance. Such information is valuable for process control, which may exploit anomaly detection from the spectral variation of froth. These observations make intuitive sense, as froths with lower fines contents exhibit stronger bitumen features and less evidence of silicate mineralogy (or heavy minerals and other contaminants).

It should be noted that other classification approaches than k-means may be used, including any classification or clustering algorithm or statistical clustering or classification method or relationship. Classifiers may be related to two classes of froth quality based on a qualitative assessment of froth colour, and fines content. Classifiers may be trained using a set of samples of known processability as assessed with a Denver cell. An unsupervised method may rank all bands, except for bands that pertain to water. A 3-band k-means method may be used based on manual selection of three spectral features that appeared to be relevant, as a supervised training method. Predictive capability of a classifier may be later assessed with a set of comparable test data that was not used for training the classification model. The key insight is that there are spectral features observable in froth and in ore that relate to physical features that are directly related to process performance, for example low bitumen content and high amounts of fine clays and silts. These features may be ranked and classified to give measures of process performance.

4.2 Solid/Bitumen Ratio (SBR)

Solid to bitumen ratio is a mass fraction. Total bitumen content may be found by the standard technique of Dean-Stark analysis. Solids fraction below the threshold particle size (such as 44 um or 3.9 um) may be found using standard lab techniques for particle size distribution such as Coulter or Microtrak light dispersion techniques from prepared samples, or sieve hydrometer.

4.2.1 Identified Spectral Features

As described in section 4, a correlation scalogram was generated between the SBR values of each froth sample and the wavelet power scalogram of the corresponding sample spectra. Wavelet powers with an absolute correlation coefficient (R) larger than 0.93 may be used. A total of 24 spectral wavelet power regions (Table 2) may be identified to be highly correlated with the SBR of froth. The representative features and their combination may be used to predict the SBR of froth.

4.2.2 Prediction Model Using 10 Samples

A combination of three wavelet powers (#4, #19, #21 in Table 2) may be used to model the relationship between SBR and wavelet power spectral data of the froth. In a particular embodiment, the statistical relationship may be generated between the analytical data (SBR) and the wavelet power data for the three features using a simple linear, multiple-regression analysis. A cross-validation was conducted to assess the standard deviation of the error for the model.

The statistical relationship details include:

Feature center position: 1715 nm (#4), 531 nm (#19), 2387 nm (#21)

p-level: 0.0036 (#4), 0.0153 (#19), 0.0381 (#21)

Multiple $R^2$: 0.9894

Standard deviation of the error: 0.18

Equation:

$$SBR = 0.87 + 2920.11 *_2P_{715\,nm} - 1664.27 *_4P_{531\,nm} - 53.01 *_5P_{2387\,nm} \quad (4)$$

($_sP_l$ denotes the wavelet power for scale s at center wavelength l)

4.3. Estimation of Sample % Bitumen and Fines

Tables 7 and 8 show the total bitumen content (% TBC) and % fines (% pp 44) estimated using the method disclosed in this document for the ten samples compare well with laboratory determined values, the ten samples falling within the predictive error of the model determined from a larger suite of modeling and validation samples. This applies to samples regardless of their froth color.

The ten samples of this study fall within the observed variability of the larger data set. The data for the ten samples were color coded as a function of the color of the froth (Table 1). This color was observed as the samples were processed in the Denver cell for extraction of oil froth by flotation in water. Most of the samples with brown froth have higher predicted % pp 3.9 fines content (and higher measured % fines, Table 1) and lower % TBC, as expected given the detection of silicate minerals features in spectra of brown froth. Samples with a dark froth are predicted to have lower % pp 3.9 fines and higher % TBC. There appears to be a % pp 3.9 threshold value of 10 separating both data populations based on froth color. Laboratory measurements of % pp 3.9 for the ten samples are required to confirm this prediction. Samples 3 and 8 represent exceptions to these observations and will require further work for explanation.

4.4. Relationship with Froth Color

Table 9 shows % TBC and sub-3.9 micron particle passing (% pp 3.9) predicted spectrally for the ten samples. These values may be compared against laboratory determined values for a larger dataset used for the modeling and validation of spectral predictive models.

5. Application to the Prediction of Ore Processability (PSB)

5.1 Identified of Spectral Features

As described in section 4, a correlation scalogram was generated between the PSB values of each ore sample and the wavelet power scalogram of the corresponding froth sample spectra.

From the correlation scalogram, wavelet powers with an absolute correlation coefficient (R) larger than 0.90 were identified. A total of 14 wavelet powers (Table 3) were identified to be highly correlated to the PSB of the samples. The representative wavelet power and their combination were used to predict the values of ore sample PSB.

5.2 Prediction Model with 10 Samples

A combination of three wavelet powers (#3, #6, #12 in Table 2) may be used to model the relationship between PSB values and wavelet power spectral data of the froth. The statistical relationship (Table 6) may be generated between the analytical data (PSB) and the wavelet power data for the 3 features using a simple linear multiple regression analysis. A cross-validation may be conducted to assess the standard deviation of errors for the model.

The statistical relationship details include:

Feature center position: 2473 nm (#3), 1713 nm (#6), 945 nm (#12)

p-level: 0.0434 (#3), 0.0279 (#6), 0.0054 (#12)

Multiple $R^2$: 0.9516

Standard deviation of the error: 0.038

Equation:

$$PSB = 0.71 - 6.47 *_5P_{2473\,nm} - 515.22 *_3P_{1713\,nm} - 569.07 *P_{945\,nm} \quad (5)$$

($_sP_l$ is denotes the wavelet power for scale s at center wavelength l)

TABLE 1

Two class classification of sample froth based on froth color and sample fines content for particles smaller than 44 microns.

| Sample # | Froth Color | Sample % Fines (% pp44) | Color ID |
|---|---|---|---|
| 1 | Brown | 31.00 | 1 |
| 2 | Very Dark | 11.13 | 0 |
| 3 | Very Brown | 27.30 | 1 |
| 4 | Brown | 40.06 | 1 |
| 5 | Very Brown | 40.75 | 1 |
| 6 | Light Brown | 46.24 | 1 |
| 7 | Very Dark | 6.71 | 0 |
| 8 | Dark | 24.98 | 0 |
| 9 | Very Dark | 13.83 | 0 |
| 10 | Very Dark | 2.44 | 0 |

TABLE 2

Spectral features identified as sensitive to the solid/bitumen ratio in froth.

| Feature ID | Scale (0-9) | R | Band center (nm) | Feature width (FWHM in nm) |
|---|---|---|---|---|
| 1 | 2 | 0.9605 | 830 | 14 |
| 2 | 2 | 0.9449 | 1085 | 8 |
| 3 | 2 | 0.977 | 1712 | 4 |
| 4 | 2 | 0.9691 | 1715 | 4 |
| 5 | 2 | 0.9338 | 1839 | 20 |
| 6 | 2 | 0.9334 | 1920 | 20 |
| 7 | 2 | 0.9748 | 2080 | 10 |
| 8 | 3 | 0.9489 | 803 | 20 |
| 9 | 3 | 0.9716 | 867 | 24 |
| 10 | 3 | 0.9713 | 1091 | 16 |
| 11 | 3 | 0.9462 | 1224 | 16 |
| 12 | 4 | 0.9744 | 822 | 32 |
| 13 | 5 | 0.95 | 848 | 64 |
| 14 | 6 | 0.9401 | 1057 | 128 |
| 15 | 2 | 0.9483 | 1235 | 8 |
| 16 | 2 | 0.9696 | 2088 | 8 |
| 17 | 3 | 0.9576 | 1180 | 16 |
| 18 | 3 | 0.9423 | 2485 | 16 |
| 19 | 4 | 0.9537 | 531 | 10 |
| 20 | 4 | 0.9344 | 1395 | 32 |
| 21 | 5 | 0.9625 | 2387 | 12 |
| 22 | 5 | 0.9604 | 2403 | 64 |
| 23 | 8 | 0.9399 | 2265 | 96 |
| 24 | 9 | 0.9312 | 2422 | 96 |

TABLE 3

Spectral features identified as sensitive to ore processability.

| Feature ID | Scale (0-9) | R | Band center (nm) | Feature width (FWHM in nm) |
|---|---|---|---|---|
| 1 | 1 | 0.9069 | 1496 | 6 |
| 2 | 2 | 0.926 | 2071 | 10 |
| 3 | 4 | 0.9038 | 2473 | 40 |
| 4 | 7 | 0.9194 | 1363 | 20 |
| 5 | 1 | 0.9155 | 1327 | 6 |
| 6 | 2 | 0.9536 | 1713 | 8 |
| 7 | 2 | 0.9168 | 1841 | 6 |
| 8 | 3 | 0.9221 | 824 | 10 |
| 9 | 3 | 0.9062 | 864 | 8 |
| 10 | 3 | 0.9389 | 951 | 6 |
| 11 | 4 | 0.9073 | 818 | 20 |
| 12 | 4 | 0.9378 | 945 | 18 |
| 13 | 5 | 0.902 | 887 | 32 |
| 14 | 6 | 0.9057 | 872 | 72 |

TABLE 4

Comparison of color, % fines, % oil and processability of the ten samples.

| Color ID | fines % | oil % | Sample # | Averaged processability |
|---|---|---|---|---|
| 0 | 13.83 | 14.15 | 9 (AN117) | 0.81 |
| 1 | 40.06 | 7.4 | 4 (AN155) | 0.61 |
| 0 | 6.71 | 11.94 | 7 (AN178f26) | 0.69 |
| 1 | 40.75 | 9.75 | 5 (AN178f96) | 0.80 |
| 0 | 11.13 | 13.85 | 2 (AN225) | 0.86 |
| 0 | 24.98 | 7.8 | 8 (AN229) | 0.75 |
| 0 | 2.44 | 13.66 | 10 (AN239) | 0.90 |
| 1 | 27.30 | 12.02 | 3 (AN397) | 0.69 |
| 1 | 46.24 | 6.97 | 6 (AQ09) | 0.28 |
| 1 | 31.00 | 8.23 | 1 (MC09) | 0.59 |

TABLE 5

Solid to bitumen ration (SBR) determined in the laboratory from Dean Stark analysis (True SBR) and the SBR predicted from the spectral model using froth spectra for the ten samples.

| True SBR from Analytical methods | Predicted SBR from froth | Visual froth color |
|---|---|---|
| 1.03 | 1.27 | Black |
| 2.64 | 2.90 | Brown |
| 0.49 | 0.33 | Black |
| 2.10 | 2.11 | Brown |
| 1.17 | 1.33 | Black |
| 1.79 | 1.79 | Black |
| 0.61 | 0.50 | Black |
| 2.59 | 2.28 | Brown |
| 6.63 | 6.56 | Brown |
| 2.14 | 2.09 | Brown |

TABLE 6

Processability (PSB) determined from the Denver Cell experiment and the Dean Stark analysis of the froth and ore samples (True PSB) and the PSB predicted using the spectral model and froth spectra for the ten samples.

| True PSB from analytical methods | Predicted PSB from froth | Dot Color |
|---|---|---|
| 0.81 | 0.81 | Black |
| 0.54 | 0.55 | Brown |
| 0.69 | 0.66 | Black |
| 0.80 | 0.81 | Brown |
| 0.86 | 0.91 | Black |
| 0.81 | 0.79 | Black |
| 0.90 | 0.82 | Black |
| 0.69 | 0.73 | Brown |
| 0.34 | 0.34 | Brown |
| 0.59 | 0.61 | Brown |

TABLE 7

Spectrally derived and experimentally measured total bitumen content (TBC) for the ten samples and for the suite of modeling and validation samples used to establish the predictive model.

| Model | | Validation | | Cosi data | |
|---|---|---|---|---|---|
| True TBC (%) | Estimated TBC (%) | True TBC (%) | Estimated TBC (%) | True TBC (%) | Estimated TBC (%) |
| 0.70 | 6.11 | 3.43 | 2.58 | 13.97 | 11.33 |
| 1.84 | 1.86 | 4.26 | 4.76 | 7.81 | 9.18 |
| 2.08 | 5.25 | 4.93 | 3.49 | 11.63 | 12.17 |
| 2.42 | 1.28 | 5.76 | 5.61 | 9.45 | 9.67 |
| 2.74 | 1.88 | 6.07 | 6.18 | 14.83 | 12.86 |
| 2.82 | 5.07 | 6.61 | 6.70 | 8.02 | 10.53 |
| 3.46 | 4.08 | 7.05 | 6.77 | 14.20 | 13.95 |
| 3.52 | 4.54 | 7.76 | 7.71 | 9.82 | 12.14 |
| 3.52 | 3.13 | 8.23 | 8.66 | 7.06 | 9.80 |
| 3.71 | 1.70 | 8.92 | 9.02 | 8.35 | 8.80 |
| 3.78 | 3.96 | 9.32 | 9.25 | | |
| 4.40 | 5.57 | 9.88 | 7.84 | | |
| 4.45 | 6.12 | 10.16 | 10.92 | | |
| 4.62 | 5.17 | 10.37 | 13.52 | | |
| 5.42 | 5.84 | 10.38 | 11.51 | | |
| 6.18 | 5.18 | 10.67 | 11.79 | | |
| 6.32 | 5.93 | 11.17 | 13.23 | | |
| 6.42 | 5.07 | 11.91 | 13.28 | | |
| 6.47 | 6.72 | 12.31 | 12.63 | | |
| 6.77 | 6.90 | 12.53 | 13.24 | | |
| 6.80 | 7.04 | 13.14 | 11.15 | | |
| 6.89 | 7.18 | 13.48 | 15.78 | | |
| 7.08 | 8.06 | 14.09 | 16.82 | | |
| 7.25 | 7.37 | 14.12 | 18.82 | | |
| 7.33 | 6.43 | 14.35 | 18.34 | | |
| 7.42 | 7.93 | 14.35 | 17.48 | | |
| 7.78 | 6.80 | 14.60 | 17.10 | | |
| 7.90 | 8.01 | 14.81 | 17.79 | | |
| 7.94 | 8.19 | 14.96 | 16.86 | | |
| 8.10 | 7.87 | 15.00 | 19.40 | | |
| 8.11 | 7.95 | 15.08 | 15.66 | | |
| 8.30 | 11.77 | 15.09 | 13.09 | | |
| 8.38 | 8.10 | 15.16 | 18.90 | | |
| 8.46 | 7.93 | 15.20 | 16.49 | | |
| 8.64 | 7.87 | 15.95 | 13.60 | | |
| 8.84 | 9.64 | 16.26 | 14.42 | | |
| 8.87 | 8.98 | 5.07 | 6.28 | | |
| 8.87 | 8.15 | 6.94 | 13.65 | | |
| 8.91 | 9.00 | 7.51 | 10.05 | | |
| 8.92 | 9.65 | 7.64 | 9.61 | | |
| 8.95 | 8.21 | 8.67 | 10.36 | | |
| 9.28 | 8.70 | 8.91 | 10.29 | | |
| 9.29 | 9.39 | 9.86 | 10.21 | | |
| 9.33 | 9.55 | 10.23 | 14.83 | | |
| 9.38 | 9.07 | 13.73 | 16.30 | | |
| 9.49 | 9.21 | 12.20 | 15.30 | | |
| 9.90 | 9.94 | 13.44 | 15.04 | | |
| 9.93 | 9.58 | 13.60 | 17.97 | | |

TABLE 7-continued

Spectrally derived and experimentally measured total bitumen content (TBC) for the ten samples and for the suite of modeling and validation samples used to establish the predictive model.

| Model | | Validation | | Cosi data | |
|---|---|---|---|---|---|
| True TBC (%) | Estimated TBC (%) | True TBC (%) | Estimated TBC (%) | True TBC (%) | Estimated TBC (%) |
| 10.33 | 10.46 | 11.41 | 12.88 | | |
| 10.37 | 9.37 | 13.98 | 14.11 | | |
| 10.77 | 12.17 | 15.46 | 20.12 | | |
| 11.09 | 9.54 | | | | |
| 11.17 | 11.75 | | | | |
| 11.33 | 9.39 | | | | |
| 11.40 | 13.21 | | | | |
| 11.72 | 9.73 | | | | |
| 11.75 | 11.28 | | | | |
| 11.77 | 12.59 | | | | |
| 11.80 | 11.99 | | | | |
| 11.87 | 11.81 | | | | |
| 11.90 | 10.47 | | | | |
| 12.38 | 14.36 | | | | |
| 12.39 | 13.99 | | | | |
| 12.68 | 14.43 | | | | |
| 12.70 | 13.29 | | | | |
| 12.77 | 12.64 | | | | |
| 12.98 | 12.63 | | | | |
| 13.12 | 12.73 | | | | |
| 13.40 | 13.39 | | | | |
| 13.47 | 10.77 | | | | |
| 13.55 | 11.87 | | | | |
| 13.56 | 15.30 | | | | |
| 13.65 | 12.53 | | | | |
| 13.87 | 13.45 | | | | |
| 14.44 | 14.76 | | | | |
| 14.49 | 13.36 | | | | |
| 14.50 | 14.76 | | | | |
| 14.71 | 15.37 | | | | |
| 14.72 | 14.55 | | | | |
| 14.86 | 14.95 | | | | |
| 15.01 | 13.63 | | | | |
| 15.47 | 13.72 | | | | |
| 15.50 | 14.04 | | | | |
| 15.63 | 12.12 | | | | |
| 16.01 | 15.65 | | | | |

TABLE 8

Spectrally derived and experimentally measured % particle passing at 44 microns (PP44) for the ten samples and for the suite of modeling and validation samples used to establish the predictive model.

| Model | | Validation | | Cosi data | |
|---|---|---|---|---|---|
| True PP44 (%) | Estimated PP44 (%) | True PP44 (%) | Estimated PP44 (%) | True PP44 (%) | Estimated PP44 (%) |
| 49.13 | 49.87 | 25.15 | 26.04 | 13.83 | 16.04 |
| 62.95 | 52.06 | 24.88 | 35.75 | 40.06 | 32.16 |
| 64.55 | 50.75 | 21.25 | 20.50 | 6.71 | −1.71 |
| 37.15 | 34.48 | 28.28 | 30.49 | 40.75 | 40.43 |
| 13.20 | 24.32 | 17.73 | 29.45 | 11.13 | 14.36 |
| 45.28 | 38.17 | 44.23 | 31.35 | 24.98 | 23.38 |
| 49.25 | 36.79 | 27.80 | 24.10 | 2.44 | 1.97 |
| 39.35 | 32.58 | 24.68 | 29.64 | 27.30 | 10.32 |
| 51.45 | 40.02 | 36.83 | 22.65 | 46.24 | 46.21 |
| 32.38 | 30.21 | 28.55 | 23.58 | 31.00 | 34.75 |
| 16.93 | 38.95 | 28.35 | 24.98 | | |
| 35.53 | 31.45 | 28.48 | 18.18 | | |
| 33.40 | 37.09 | 17.45 | 17.80 | | |
| 38.55 | 36.57 | 2.47 | −4.05 | | |
| 25.20 | 33.91 | 12.31 | 7.94 | | |
| 26.60 | 27.93 | 16.55 | 5.75 | | |
| 17.18 | 29.42 | 30.07 | 34.36 | | |
| 21.75 | 29.04 | 32.37 | 29.34 | | |
| 24.00 | 24.87 | 29.00 | 31.20 | | |
| 18.08 | 20.06 | 35.73 | 28.27 | | |
| 21.38 | 26.34 | 19.97 | 15.47 | | |
| 17.33 | 24.20 | 25.23 | 23.84 | | |
| 9.05 | 12.98 | 31.40 | 25.46 | | |
| 14.00 | 22.49 | 21.60 | 21.66 | | |
| 8.61 | 9.06 | 17.53 | 21.05 | | |
| 8.37 | 7.69 | 24.38 | 29.67 | | |
| 11.68 | 14.90 | 17.19 | 27.98 | | |
| 7.27 | 7.03 | 7.85 | 19.52 | | |
| 7.32 | 8.07 | 7.30 | 9.02 | | |
| 7.07 | 9.00 | 5.12 | −0.60 | | |
| 15.05 | 12.65 | 1.49 | −1.84 | | |
| 7.45 | 9.37 | 2.38 | −0.20 | | |
| 3.92 | 1.84 | 11.18 | 4.19 | | |
| 33.33 | 18.55 | 1.55 | 0.76 | | |
| 13.45 | 12.42 | 1.71 | 1.70 | | |
| 6.24 | 4.84 | 1.20 | 4.94 | | |
| 8.34 | 10.90 | 1.96 | 2.75 | | |
| 4.58 | 4.14 | 53.38 | 51.40 | | |
| 5.16 | 2.83 | 7.00 | 30.52 | | |
| 59.45 | 54.60 | 28.94 | 33.89 | | |
| 60.28 | 57.00 | 28.33 | 37.39 | | |
| 54.75 | 52.48 | 22.51 | 35.47 | | |
| 16.83 | 21.49 | 21.76 | 28.97 | | |
| 56.78 | 50.72 | 37.34 | 43.60 | | |
| 60.85 | 53.81 | 18.02 | 22.80 | | |
| 53.60 | 52.51 | 9.03 | 9.73 | | |
| 44.83 | 38.31 | 16.64 | 16.44 | | |
| 29.80 | 30.53 | 7.66 | 19.41 | | |
| 57.73 | 51.23 | 3.76 | 6.20 | | |
| 51.28 | 50.16 | 8.66 | 30.57 | | |
| 11.43 | 14.61 | 5.38 | 9.80 | | |
| 40.53 | 30.88 | 1.66 | −5.22 | | |
| 44.23 | 37.38 | | | | |
| 47.43 | 44.43 | | | | |
| 37.95 | 23.48 | | | | |
| 31.78 | 22.72 | | | | |
| 39.23 | 39.10 | | | | |
| 39.95 | 31.80 | | | | |
| 34.58 | 29.24 | | | | |
| 10.90 | 24.96 | | | | |
| 10.25 | 7.73 | | | | |
| 22.58 | 25.94 | | | | |
| 16.75 | 16.69 | | | | |
| 13.40 | 17.50 | | | | |
| 13.98 | 14.52 | | | | |
| 24.13 | 22.81 | | | | |
| 10.50 | 9.36 | | | | |
| 7.28 | 7.06 | | | | |
| 3.32 | 5.21 | | | | |

TABLE 9

Total bitumen content (true oil %) and particle passing at 3.9 microns (PP3.9) derived spectrally for the ten samples and laboratory determined for modeling samples used to establish the predictive model.

| Model | | Cosi data | | |
|---|---|---|---|---|
| True oil (%) | PP3.9 (%) | True oil (%) | PP3.9 (%) | Froth Color |
| 0.7000 | 20.65 | 13.97 | 5.40 | Black |
| 1.8425 | 16.18 | 7.81 | 11.71 | Brown |
| 2.0775 | 23.28 | 11.63 | −1.32 | Black |
| 2.4150 | 19.90 | 9.45 | 13.38 | Brown |
| 2.7425 | 18.38 | 14.83 | 8.23 | Black |
| 2.8175 | 7.20 | 8.02 | 7.80 | Black |

TABLE 9-continued

Total bitumen content (true oil %) and particle passing at 3.9 microns (PP3.9) derived spectrally for the ten samples and laboratory determined for modeling samples used to establish the predictive model.

| Model | | Cosi data | | |
|---|---|---|---|---|
| True oil (%) | PP3.9 (%) | True oil (%) | PP3.9 (%) | Froth Color |
| 3.4625 | 18.33 | 14.20 | 5.80 | Black |
| 3.5175 | 19.58 | 9.82 | 1.37 | Brown |
| 3.5200 | 18.30 | 7.06 | 16.99 | Brown |
| 3.7050 | 17.15 | 8.35 | 12.63 | Brown |
| 3.7800 | 15.15 | | | |
| 4.4000 | 11.32 | | | |
| 4.4500 | 6.71 | | | |
| 4.6200 | 8.53 | | | |
| 5.4150 | 18.28 | | | |
| 6.1800 | 12.78 | | | |
| 6.3225 | 14.08 | | | |
| 6.4225 | 17.80 | | | |
| 6.4675 | 11.90 | | | |
| 6.7725 | 4.27 | | | |
| 6.8025 | 14.65 | | | |
| 6.8875 | 14.28 | | | |
| 7.0750 | 13.03 | | | |
| 7.2475 | 14.33 | | | |
| 7.3250 | 8.83 | | | |
| 7.4150 | 10.28 | | | |
| 7.7800 | 5.28 | | | |
| 7.9025 | 13.80 | | | |
| 7.9375 | 11.55 | | | |
| 8.1000 | 17.90 | | | |
| 8.1125 | 6.71 | | | |
| 8.3000 | 14.90 | | | |
| 8.3750 | 13.25 | | | |
| 8.4550 | 13.23 | | | |
| 8.6425 | 14.30 | | | |
| 8.8400 | 11.03 | | | |
| 8.8675 | 7.72 | | | |
| 8.8700 | 9.49 | | | |
| 8.9125 | 13.15 | | | |
| 8.9150 | 9.26 | | | |
| 8.9450 | 10.31 | | | |
| 9.2750 | 11.19 | | | |
| 9.2900 | 6.03 | | | |
| 9.3250 | 10.94 | | | |
| 9.3750 | 10.75 | | | |
| 9.4850 | 12.88 | | | |
| 9.8950 | 13.10 | | | |
| 9.9300 | 10.85 | | | |
| 10.3300 | 11.30 | | | |
| 10.3675 | 11.73 | | | |
| 10.7675 | 10.06 | | | |
| 11.0900 | 3.65 | | | |
| 11.1675 | 11.09 | | | |
| 11.3275 | 9.45 | | | |
| 11.4000 | 10.23 | | | |
| 11.7225 | 4.44 | | | |
| 11.7500 | 3.65 | | | |
| 11.7725 | 7.47 | | | |
| 11.7975 | 6.83 | | | |
| 11.8675 | 5.16 | | | |
| 11.9025 | 5.74 | | | |
| 12.3800 | 0.89 | | | |
| 12.3850 | 4.75 | | | |
| 12.6775 | 4.69 | | | |
| 12.7000 | 3.09 | | | |
| 12.7725 | 3.09 | | | |
| 12.9825 | 4.21 | | | |
| 13.1200 | 2.56 | | | |
| 13.4000 | 5.24 | | | |
| 13.4725 | 2.62 | | | |
| 13.5500 | 8.46 | | | |
| 13.5600 | 2.58 | | | |
| 13.6525 | 6.07 | | | |
| 13.8650 | 2.75 | | | |
| 14.4425 | 6.19 | | | |
| 14.4925 | 3.60 | | | |
| 14.4950 | 1.49 | | | |
| 14.7075 | 10.19 | | | |
| 14.7200 | 4.33 | | | |
| 14.8625 | 2.04 | | | |
| 15.0125 | 2.76 | | | |
| 15.4700 | 3.09 | | | |
| 15.4975 | 1.67 | | | |
| 15.6300 | 1.37 | | | |
| 16.0100 | 1.88 | | | |

TABLE 10

K-mean classification of the wavelet power at 937 nm, 2160 nm, and 2200 nm for the ten samples.

| Band 588 | Band 1811 | Band 1851 | Froth Color |
|---|---|---|---|
| −0.007 | 0.116 | 0.145 | Dark |
| 0.001 | 0.067 | 0.061 | Brown |
| −0.012 | 0.245 | 0.473 | Dark |
| −0.002 | 0.086 | 0.085 | Brown |
| −0.008 | 0.109 | 0.145 | Dark |
| −0.007 | 0.144 | 0.168 | Dark |
| −0.010 | 0.136 | 0.206 | Dark |
| −0.002 | 0.082 | 0.079 | Brown |
| 0.004 | 0.119 | 0.103 | Brown |
| 0.000 | 0.133 | 0.152 | Brown |

TABLE 11

Average processability analytically determined using Dean Stark analysis of the ten samples.

| Sample ID | Average Processability | Dot Color |
|---|---|---|
| 1 | 0.59 | Brown |
| 2 | 0.86 | Black |
| 3 | 0.69 | Brown |
| 4 | 0.61 | Brown |
| 5 | 0.80 | Brown |
| 6 | 0.28 | Brown |
| 7 | 0.69 | Black |
| 8 | 0.75 | Black |
| 9 | 0.81 | Black |
| 10 | 0.90 | Black |

TABLE 12

Processability analytically determined using Dean Stark analysis of the ten samples in four experiments.

| | Processability | | | |
|---|---|---|---|---|
| Sample ID | Experiment 1 | Experiment 2 | Experiment 3 | Experiment 4 |
| 1 | 0.59 | 0.72 | 0.41 | 0.63 |
| 2 | 0.77 | 0.84 | 0.93 | 0.90 |
| 3 | 0.80 | 0.71 | 0.61 | 0.63 |
| 4 | 0.43 | 0.82 | 0.62 | 0.58 |
| 5 | 0.83 | 0.77 | 0.86 | 0.74 |
| 6 | 0.17 | 0.26 | 0.45 | 0.24 |
| 7 | 0.68 | 0.65 | 0.75 | 0.70 |

TABLE 12-continued

Processability analytically determined using Dean Stark analysis of the ten samples in four experiments.

| Sample ID | Processability | | | |
|---|---|---|---|---|
| | Experiment 1 | Experiment 2 | Experiment 3 | Experiment 4 |
| 8 | 0.87 | 0.76 | 0.87 | 0.51 |
| 9 | 0.75 | 0.79 | 0.91 | 0.81 |
| 10 | 0.87 | 0.89 | 0.93 | 0.93 |

TABLE 13

Predicted percentage of fines passing 3.9 um filter (pp3.9) using wavelet analysis and true percentage of fines passing 3.9 um filter for the ten samples.

| Predicted pp3.9 from ore spectra (%) | True PP3.9 from ore solids (%) |
|---|---|
| 5.40 | 2.26 |
| 11.71 | 7.77 |
| −1.32 | 0.54 |
| 13.38 | 6.31 |
| 8.23 | 1.93 |
| 7.80 | 5.98 |
| 5.80 | 0.99 |
| 16.99 | 9.43 |
| 12.63 | 13.41 |

TABLE 14

Percent particle passing at 44 microns (PP44) in ore, total bitumen content (TBC) and solids/bitumen ratio in froth for the ten samples.

| PP44 (%) in homogenized ore | Sample ID | TBC (%) | solids/bitumen ratio in froth | Froth color |
|---|---|---|---|---|
| 31.00 | 1 | 8.35 | 2.14 | Brown |
| 11.13 | 2 | 14.83 | 1.17 | Black |
| 27.30 | 3 | 9.82 | 2.59 | Brown |
| 40.06 | 4 | 7.81 | 2.64 | Brown |
| 40.75 | 5 | 9.45 | 2.10 | Brown |
| 46.24 | 6 | 7.06 | 6.63 | Brown |
| 6.71 | 7 | 11.63 | 0.49 | Black |
| 24.98 | 8 | 8.02 | 1.79 | Black |
| 13.83 | 9 | 13.97 | 1.03 | Black |
| 2.44 | 10 | 14.20 | 0.61 | Black |

TABLE 15

Percent particle passing at 44 microns (PP44) in ore, total bitumen content (TBC) and % bitumen in froth for the ten samples.

| PP44 (%) in homogenized ore | Sample ID | TBC (%) | % bitumen in froth | Froth color |
|---|---|---|---|---|
| 31.00 | 1 | 8.35 | 5.63 | Brown |
| 11.13 | 2 | 14.83 | 14.44 | Black |
| 27.30 | 3 | 9.82 | 6.27 | Brown |
| 40.06 | 4 | 7.81 | 6.11 | Brown |
| 40.75 | 5 | 9.45 | 8.63 | Brown |
| 46.24 | 6 | 7.06 | 2.54 | Brown |
| 6.71 | 7 | 11.63 | 21.52 | Black |
| 24.98 | 8 | 8.02 | 10.02 | Black |
| 13.83 | 9 | 13.97 | 17.65 | Black |
| 2.44 | 10 | 14.20 | 28.96 | Black |

TABLE 16

Ore processability, total bitumen content (TBC) and solids/bitumen ratio in froth for the ten samples.

| Ore processability | Sample ID | TBC (%) | solids/bitumen ratio in froth | Froth color |
|---|---|---|---|---|
| 0.59 | 1 | 8.35 | 2.14 | Brown |
| 0.86 | 2 | 14.83 | 1.17 | Black |
| 0.69 | 3 | 9.82 | 2.59 | Brown |
| 0.61 | 4 | 7.81 | 2.64 | Brown |
| 0.80 | 5 | 9.45 | 2.10 | Brown |
| 0.28 | 6 | 7.06 | 6.63 | Brown |
| 0.69 | 7 | 11.63 | 0.49 | Black |
| 0.79 | 8 | 8.02 | 1.79 | Black |
| 0.81 | 9 | 13.97 | 1.03 | Black |
| 0.90 | 10 | 14.20 | 0.61 | Black |

TABLE 17

Ore processability, total bitumen content (TBC) and % bitumen in froth for the ten samples.

| Ore processability | Sample ID | TBC (%) | % bitumen in froth | Froth color |
|---|---|---|---|---|
| 0.59 | 1 | 8.35 | 5.63 | Brown |
| 0.86 | 2 | 14.83 | 14.44 | Black |
| 0.69 | 3 | 9.82 | 6.27 | Brown |
| 0.61 | 4 | 7.81 | 6.11 | Brown |
| 0.80 | 5 | 9.45 | 8.63 | Brown |
| 0.28 | 6 | 7.06 | 2.54 | Brown |
| 0.69 | 7 | 11.63 | 21.52 | Black |
| 0.79 | 8 | 8.02 | 10.02 | Black |
| 0.81 | 9 | 13.97 | 17.65 | Black |
| 0.90 | 10 | 14.20 | 28.96 | Black |

REFERENCES CITED

1. Lyder, D., Feng, J. Rivard, B., Gallie, A., and Cloutis, E., "Remote bitumen content estimation of Athabasca oil sand from hyperspectral infrared reflectance spectra using Gaussian singlets and derivative of Gaussian wavelets", Fuel 89: 760-767, 2010.
2. Feng, J., Rivard, B., Gallie, A., and Cloutis, E., "Feature selection and broad band bitumen content estimation of Athabasca oil sand from infrared reflectance spectra", IEEE Workshop on Hyperspectral image and signal processing: evolution of remote sensing. 26-28 Aug., 2009, Grenoble, France, 2009.
3. Cheng, T, Rivard, B., Sanchez-Azofeifa, A. 2011. Spectroscopic determination of leaf water content using continuous wavelet analysis. Rem. Sens. Environm. 115: 659-670.
4. Rivard, B., Feng, J., Gallie, A., and Sanchez-Azofeifa, A. 2008. Continuous wavelets for the improved use of spectral libraries and hyperspectral data. Rem. Sens. Environ. 112: 2850-2862.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The invention claimed is:

1. A method of processing ore froth, the method comprising:
obtaining a reflectance spectra of an ore froth using a camera;

applying a calculation to the reflectance spectra to generate a value representative of the reflectance spectra of the ore froth;

classifying the quality of the ore froth using the value; and using the classification of the quality of the ore froth in ore froth processing.

2. The method of claim 1 in which the ore comprises bitumen ore.

3. The method of claim 2 in which the property of the reflectance spectra comprises one or more of solid to bitumen ratio, total bitumen content, fines content, processability and color.

4. The method of claim 1 in which applying a calculation to the reflectance spectra comprises:

applying a wavelet decomposition to the reflectance spectra for one or more wavelengths and one or more scales to obtain wavelet powers corresponding to the one or more wavelengths and the one or more scales;

calculating a value for a property of the reflectance spectra using a statistical relationship between the one or more wavelet powers and the property of the reflectance spectra.

5. The method of claim 4 in which the one or more wavelet powers used in the statistical relationship is in a correlation with the property of the reflectance spectra, the one or more wavelet powers used in the statistical relationship being correlated with the property of the reflectance spectra.

6. The method of claim 5 in which the correlation is determined by calculating a Pearson linear correlation coefficient for each wavelet power between each wavelet power and the property of the reflectance spectra.

7. The method of claim 6 in which applying a calculation to the reflectance spectra further comprises continuum removal of the reflectance spectra.

8. The method of claim 5 in which the statistical relationship between the one or more wavelet powers and the property of the reflectance spectra comprises a linear relationship.

9. The method of claim 8 in which the linear relationship is predetermined by using a linear multiple regression analysis between analytical laboratory data of the property, and a set of comparable sample data of the property.

10. The method of claim 4 in which the statistical relationship between the one or more wavelet powers and the property of the reflectance spectra is determined by applying a cluster analysis to the set of comparable sample data of the property, the cluster analysis classifying the comparable sample data of the property into categories of the property, one or more wavelet powers being an element of the set of comparable sample data of the property.

11. The method of claim 10 in which the cluster analysis comprises a K-mean classifier.

12. The method of claim 4 in which the wavelet decomposition uses for a mother wavelet basis a negative normalized second derivative of a Gaussian function.

13. The method of claim 1 in which the camera obtains one or more of infrared wavelength reflectance spectra, visible wavelength reflectance spectra, and visible wavelength reflectance spectra and infrared wavelength reflectance spectra.

14. The method of claim 1 in which the reflectance spectra comprises an average of a set of several reflectance spectra.

15. The method of claim 1 in which the reflectance spectra is obtained from ore froth in a separation cell, in a gravity settler, in a mechanical flotation cell, in a hydrocyclone, in a separation unit that delivers ore froth to an intermediate holding tank, or withdrawn from a slipstream from a hydrotransport line.

16. The method of claim 1 in which using the classification of the quality of the ore froth in froth processing results in any one or more of the following actions: adding additional reagents, adding additional air, changing froth underwash conditions, adding additional dilution water, recirculating low-quality froth back to a primary separation cell, reducing feed to increase residence time, or rejecting off-specification waste soil.

17. Ore processing apparatus, comprising:

a camera directed towards a vessel containing ore froth for obtaining a reflectance spectra from the ore froth;

a computer apparatus configured as a classifier for applying a calculation to the reflectance spectra to generate a value representative of the reflectance spectra of the ore froth and classifying the quality of the ore froth using the value; and a display for displaying the value.

18. Ore processing apparatus of claim 17, further comprising a process control unit responsive to the computer apparatus for altering processing of the ore froth.

19. A method of monitoring ore froth processing, the method comprising:

obtaining a reflectance spectra of an ore froth using a camera;

applying a calculation to the reflectance spectra to generate a value representative of the reflectance spectra of the ore froth;

classifying the quality of the ore froth using the value to generate an output; and displaying the output to a user.

* * * * *